United States Patent [19]

Poggi et al.

[11] Patent Number: 4,645,509
[45] Date of Patent: Feb. 24, 1987

[54] PROSTHETIC FOOT HAVING A CANTILEVER SPRING KEEL

[75] Inventors: Donald L. Poggi, Bainbridge Island; Ernest M. Burgess, Mercer Island; David E. Moeller, Bainbridge Island; Drew A. Hittenberger, Seattle, all of Wash.

[73] Assignee: Model & Instrument Development Corporation, Seattle, Wash.

[21] Appl. No.: 619,190

[22] Filed: Jun. 11, 1984

[51] Int. Cl.[4] ............................................. A61F 2/60
[52] U.S. Cl. ........................................ 623/55; 623/53
[58] Field of Search ............... 3/5, 6, 7, 2, 4, 6.1; 623/53, 54, 55, 27, 28, 47, 48, 49, 50, 51, 52

[56] References Cited

U.S. PATENT DOCUMENTS

| | | | |
|---|---|---|---|
| 2,075,583 | 3/1937 | Lange | 3/8 |
| 3,335,428 | 8/1967 | Gajdos | 3/7 |
| 3,754,286 | 8/1973 | Ryan | 623/55 |
| 3,833,941 | 9/1974 | Wagner | 3/7 |
| 3,874,004 | 4/1975 | May | 3/7 X |
| 3,890,650 | 6/1975 | Prahl | 3/7 |
| 4,091,472 | 5/1978 | Daher et al. | 3/7 |
| 4,177,525 | 12/1979 | Arbogast et al. | 3/7 |
| 4,180,872 | 1/1980 | Chaikin | 3/7 |
| 4,225,982 | 10/1980 | Cochrane et al. | 3/7 |
| 4,302,856 | 12/1981 | May | 3/7 X |
| 4,306,320 | 12/1981 | Delp | 3/6.1 |
| 4,328,594 | 5/1982 | Campbell et al. | 3/7 |
| 4,360,931 | 11/1982 | Hampton | 3/7 X |
| 4,547,913 | 10/1985 | Phillips | 623/27 |

OTHER PUBLICATIONS

"Copes/Bionic Ankle"-Brochure, Nov. 1985.
"The Seattle Prosthetic Foot-A Design for Active Sports: Preliminary Studies", Ernest M. Burgess, M.D., et al., *Orthotics and Prosthetics Journal*, vol. 37, No. 1, Spring 1983.

Primary Examiner—Richard J. Apley
Assistant Examiner—Alan W. Cannon
Attorney, Agent, or Firm—Larry A. Jackson

[57] ABSTRACT

In a prosthetic foot constructed to store strain energy as the foot reacts to the load of the amputee's body during walking, running, jumping, etc., and then to release the stored energy to create foot lift and thrust which complements the user's natural stride, a monolithic cantilever beam made of a hardened polymer is provided as the keel of the foot with an ankle attachment fitting for connection to a standard upper prosthesis. A flexible foamed polymer is molded about the keel, in the shape of a natural foot, to transfer horizontal loads to the keel and to serve as a cosmetic cover.

26 Claims, 12 Drawing Figures

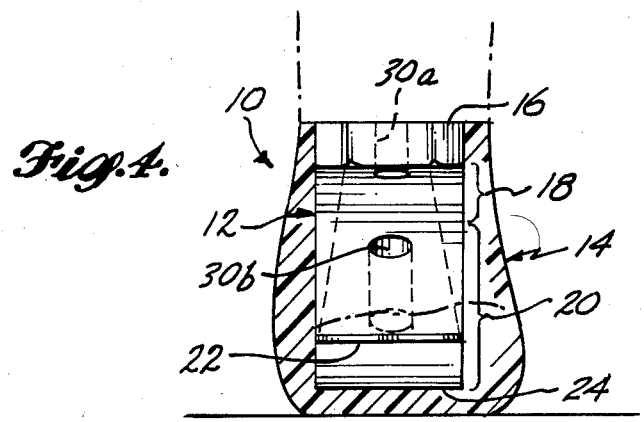
Fig. 4.
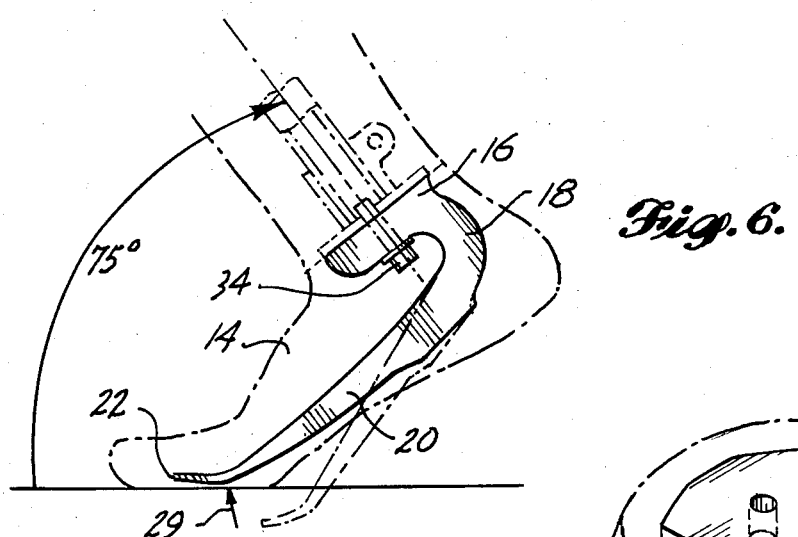
Fig. 6.
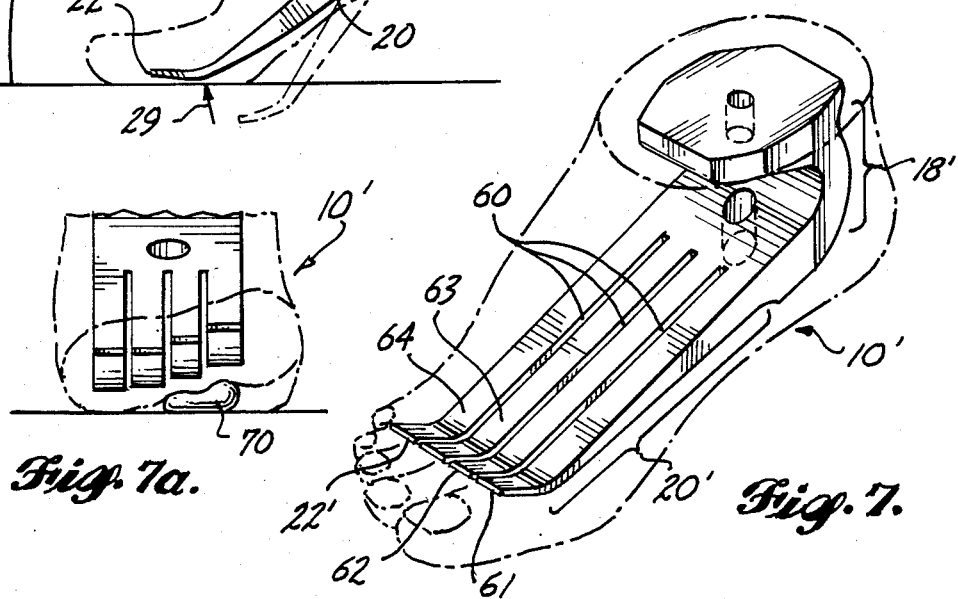
Fig. 7a.
Fig. 7.

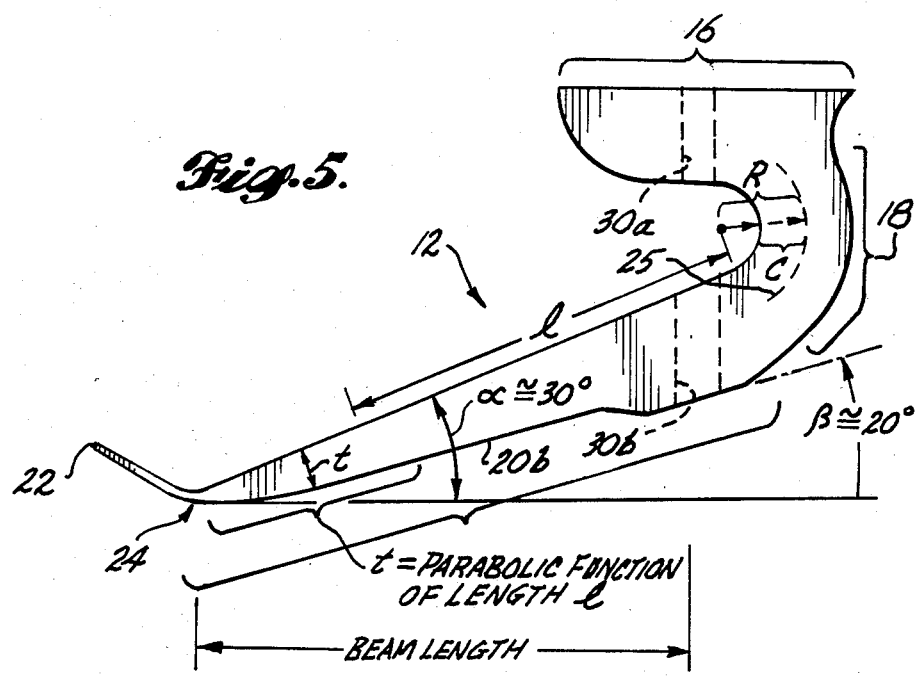
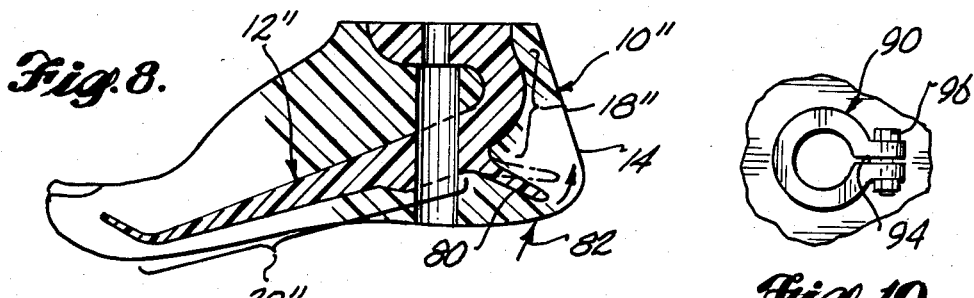
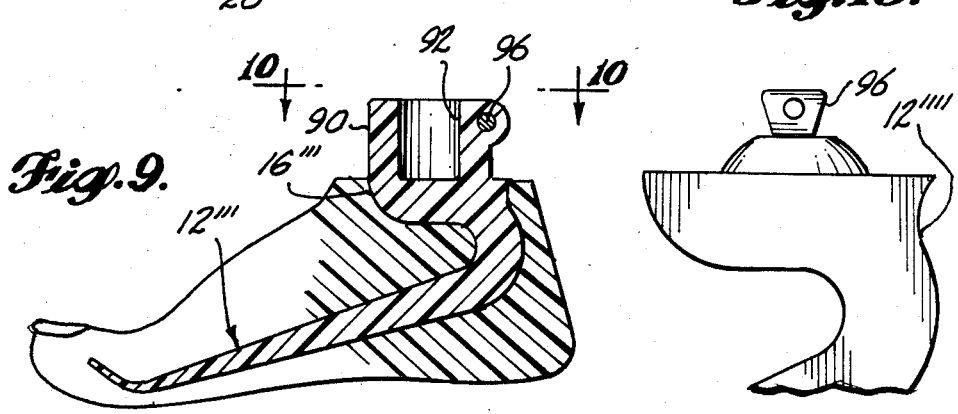
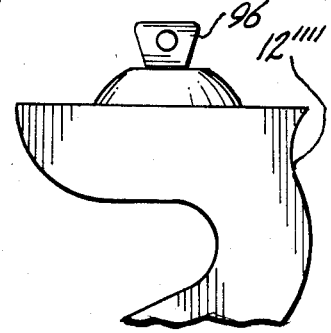

PROSTHETIC FOOT HAVING A CANTILEVER SPRING KEEL

This invention was made with the support of the United States Government. Pursuant to Title 35 U.S.C., Section 202, this gives notice that the Government has certain rights in the invention when used for Government purposes.

BACKGROUND OF THE INVENTION

The invention relates to a prosthetic foot of the energy-storing type, and a method of manufacturing same.

Until recently, prosthetic feet, ankles and lower legs available to lower limb amputees, have been primarily designed for walking and, hence, the structure of such conventional prostheses have failed to provide a natural lift and thrust effect for the more active and sports-minded person. Although some foot prostheses contain a form of energy absorption, such as various forms of metal springs or flexible foam located in the heel region, e.g., the "solid ankle cushion heel" or SACH foot, such devices do little more than absorb some of the pistoning or shock forces that would otherwise be transmitted to the amputee's stump. For walking, such prior art devices are at least acceptable; however, when the amputee attempts to walk briskly, or over long distances, run and jump, then the prosthesis has the feel of a "dead" foot lacking a natural quality of rebound or springback, and forward thrust necessary for athletic movement. As a result, excessive energy is required by the user to carry the foot along at an unnatural and, hence, uncomfortable gait.

Efforts have been made to construct a prosthetic foot that interacts dynamically with the cyclic loading and unloading of the foot by the amputee's body motions. One such prosthesis is known as the "FLEX-FOOT" manufactured by Flex-Foot, Inc., Salt Lake City, Utah, and comprises a combination lower leg and foot prosthesis in which the main structural member is made of aerospace graphite composites. The energy storage in the "FLEX-FOOT" prosthesis occurs in an elongate shaft portion extending upward from a midbody point of an enlarged foot portion, which also stores energy, and joining an enlarged upper prosthesis adapted for attachment to the stump. Such a prosthesis has advantages in overcoming some of the problems found in nonenergy-storing devices, however, the required elongate shaft portion extending between the foot and the upper prosthesis renders this device unusable when only a foot prosthesis is required, and when it is necessary or desirable to attach just a foot prosthesis to a standard lower leg fitting. Prosthesis modularity is important in accommodating the needs of a widely varying range of patient requirements.

One earlier attempt to provide a foot prosthesis that overcomes the above problems was made by a group headed by Dr. Ernest M. Burgess, one of the co-inventors herein, and is disclosed in a paper entitled "The Seattle Prosthetic Foot" appearing in *Orthotics and Prosthetics Journal,* Vol. 37, No. 1, Spring 1983. In that article, a prosthetic foot structure comprises a layup of fiberglass leaf springs in the shape of a cantilever structure with the secured end of the cantilever being joined or fastened to an upper prosthesis. The leaf springs, which are laminated, form a V-shaped bend between an attachment flange and a main forefoot portion, and a rubber deflection bumper is disposed in the "V" to cushion the compression of the "V" immediately under the point of attachment to the upper prosthesis. A cable connected between the attachment flange and the series of leaf springs prevents excessive extension (divergence of the "V" between the attachment flange and the leaf springs), and thereby minimizes the tendency of the structure to delaminate under certain use conditions. While testing of this early experimental foot showed promise, the structure itself was too heavy for most patients and the laminated spring structure did not prove sufficiently durable in service. Users also complained that the stiffness of the foot made slow walking difficult. The laminated epoxy/glass leaf spring design required considerable, direct assembly labor, and the adhesive bonding of the laminated structure added cost, weight and was the primary cause of the lack of durability of the foot.

SUMMARY OF THE INVENTION

The prosthetic foot, in accordance with the present invention, comprises a monolithic cantilever keel made of a hardened polymer or polymers and that has an attachment flange at the center of the ankle for fastening to a standard upper prosthesis, a uniformly curved strain energy-storing heel portion that is integrally joined to the rear of the attachment flange and is relatively thickened and arranged to extend in transition first downward and rearward, and to then curve at a radius R, selected commensurate with the thickness to maintain a uniform stress, to a downward and foward direction where the keel straightens and extends as a forefoot portion, terminating at a toe end. The polymer or polymers, which may be reinforced by fibers, are selected to provide a mix of viscous and elastic properties, as well as a suitable flexural modulus so that the keel deflects sufficiently in reaction to the footfall, and the resultant strain energy is stored in the forefoot and heel portions and then released at a natural time and in a combined forward (thrust) and upward (lift) direction which reduces the energy expended by the user and complements the person's gait cycle. The configuration of the keel is such as to provide substantially uniform stress throughout, especially in the curvature of the heel portion, so as to minimize fatigue damage to the polymer material with the least possible keel size and, hence, least weight.

The keel is covered by a flexible, foamed polymer material of substantially lower density than the keel. This cover is bonded to the exterior surface of the monolithic keel and is molded to the shape of a foot. The foamed polymer cover serves to cushion heel strike shocks and, when compressed, transfers loads, especially horizontal loads, between the keel and ground, shoe, sock or other footwear. Additionally, the foamed polymer cover is cosmetic.

In a preferred embodiment, the forefoot portion of the keel is of a generally uniform width and, in thickness, has a parabolic taper between the heel portion and toe end. An angled upturn of the keel forefoot is provided at the toe end to minimize the required deflection angle and, hence, stress on the keel during toe flexure, and also to provide a vertical component in the keel-to-foam cover bond to assist in transferring horizontal loads from the exterior of the foam cover to the keel with a minimum cover-to-keel bond line stress.

By these features, a prosthetic foot is provided which overcomes those characteristics present in prior art prosthetics which severely restricted normal running and other strenuous, athletic activities and, to a lesser but still significant extent, placed limitations on such activities as long walks and climbing stairs. The unique structure of the foot is highly efficient in accommodating the necessary loads and does so with a minimal number of components, for reduced manufacturing costs, and a minimum number of internal joints, for reduced risk of mechanical failure. The weight of the foot is not significantly greater than the industry standard SACH foot and is substantially less than most other prosthesis which have attempted to provide an energy storage feature. The foot is compatible with industry standard fittings, to allow adaptability and adjustability in the fitting of a patient by the prosthetist.

In an alternative embodiment, the forefoot portion of the keel is slit lengthwise from the toe end toward the heel portion to form two or more independently deflectable toe-like segments that provide improved stability on uneven terrain and afford some freedom of deflection of the forefoot portion which simulates a natural side-to-side rotation of the foot in the horizontal plane. Another alternative embodiment comprises forming the monolithic keel with a heel spur of the same hardened polymer or polymers. The heel spur extends generally downward and rearward from the heel portion and provides an auxiliary energy storage and recovery from heel strike, and adds stiffness to the foot when using very light and soft foamed polymers as the cover material.

Alternate forms of the attachment fittings include through bores in the attachment and forefoot portions of the keel and registering portions of the foamed cover for receiving an industry standard attachment bolt, and an integrally formed stub or collar for directly accommodating standard prosthetic fittings such as a tubular pylon or other prosthetic hardware.

To provide a complete disclosure of the invention, reference is made to the appended drawings and following description of preferred and alternative embodiments.

BRIEF DESCRIPTION OF THE DRAWINGS

FIG. 4 is a front sectional view of the foot, taken along the plane indicated by section line 4—4 of FIG. 3.

FIG. 5 shows an enlarged, detailed view of the monolithic keel of the foot, and illustrates the parabolic taper of the forefoot between the heel portion and the toe end.

FIG. 6 is a side elevational view, showing the foot as strained in use and indicating, by the moved position shown in dotted lines, the deflection and energy storage of the keel when the ball of the foot strikes the ground.

FIG. 7 is an isometric view similar to FIG. 1, but showing an alternative embodiment of the prosthetic foot in which the forefoot portion of the keel is split into a plurality of toe-like segments for added flexibility and stability.

FIG. 7a is front elevational view of the action of the split toe-like segments of the embodiment of FIG. 7, illustrating the independent deflection of the toe-like segments.

FIG. 8 is a sectional view, similar to FIG. 2, but showing an alternative embodiment of the foot in which the monolithic keel includes an integral heel spur, wherein the undeflected, normal configuration of the spur is indicated by solid lines, and a deflected and energy storing position is indicated by the dotted lines in the figure.

FIG. 9 is a sectional view, similar to FIG. 2, and showing an alternative embodiment of the keel formed with an integral, split collar fitting for receiving a standard prosthetic pylon.

FIG. 10 is a top plan view of that portion of FIG. 9 which includes the integral split collar fitting.

FIG. 11 is a side elevation view of a further alternative embodiment having an attachment stub on the keel flange.

DETAILED DESCRIPTION OF PREFERRED AND ALTERNATE EMBODIMENTS

Figure 1:
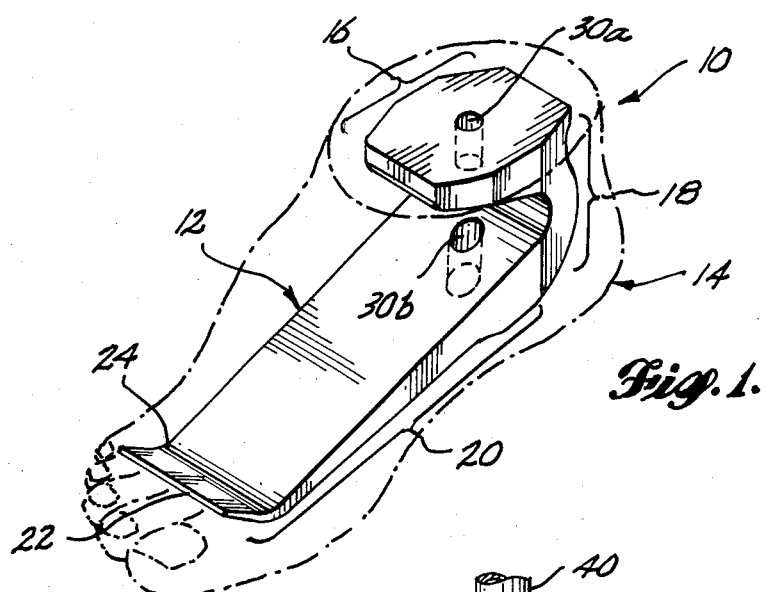
FIG. 1 is an isometric view of the preferred embodiment of the prosthetic foot and monolithic keel; the foamed polymer cover is indicated by dotted lines.

With reference to FIGS. 1 through 6, showing the preferred embodiment, a prosthetic foot 10 comprises a monolithic, hardened polymer keel 12 encased in a low-density, foamed polymer cover 14 molded to the shape of a natural foot. Keel 12 is formed and attached to an upper prosthesis, so as to function as a cantilever, and the material from which keel 12 is made and its shape are selected to provide a dampened spring effect, such that each footfall causes strain energy to be stored within the keel and then recovered in a timed spring-back or restoration that complements the user's natural stride. For this purpose, monolithic keel 12 has an ankle attachment flange 16, a heel transition portion 18, and a forefoot portion 20 that extends between heel portion 18 and a toe end 22. Flange 16 is generally of a flattened shape, roughly rectangular in the horizontal plane and, when attached to the upper prosthesis, assumes a generally horizontal orientation at a position corresponding to the upper ankle of a natural foot. An elongate and uniformly curved, and relatively thickened heel portion extends from a mid to rear area of flange 16, first downward and rearward, and then uniformly curving at a substantially constant, relatively large radius R (see FIG. 5) to a downward and forward direction. Integrally continuing from heel portion 18 is the forefoot portion 20, which is of substantially uniform width and has a parabolic tapered thickness t, as a function of the length l of portion 20. For the greatest part of the length l of forefoot portion 20, the upper surface 20a extends downward and forward at a constant slope $\alpha$ roughly equal to 30 degrees. The lower surface 20b of forefoot portion 20 begins with a substantially constant slope $\beta$, approximately equal to 20 degrees near heel portion 18, but changes to a parabolically curved surface to conform to the above-mentioned parabolic tapered thickness t adjacent the toe end of forefoot portion 20. A toe break 24 is provided in the tapered forefoot 20 where the tapering keel is bent along a widthwise line to angle upward and forward to a terminal edge at toe end 22.

Critical to the invention, keel 12 must be of a monolithic construction, either cast, molded or machined as a single piece without seams or joints, and the shape of the keel must be carefully configured to provide uniform stress throughout its body, especially in the curved region of heel portion 18. The hardened polymer or polymers from which the keel is made must possess the following properties. First, the material must exhibit a mix of elastic and viscous properties so that the deflection (see FIG. 6) and restoration of the keel under the cyclic loading of footfall and footrise has a timed or lagging stress versus yield relationship, which has been found to best simulate action of a natural foot. Secondly, because of the large stresses placed on the keel and the number of cycles of loading and unloading that occur during normal use, only a handful of those polymers exhibiting the other required properties afford the need fatigue strength, including acetal homopolymer (available from DuPont Corporation under the trademark Delrin); polyether ether ketone (also known as PEEK); and polyamide-imide (sold under the trademark Torlon). These materials also have a third essential property of moderate but not excessive flexural modulus, so that for a keel having a sufficient cross section to stand up under the stress levels and cycling expected for average use, the keel will deflect through one to two inches under 200 to 450 pound loads. A deflection within this range, under these load conditions, has been found necessary to store and release sufficient energy from the foot to assist the user. The flexural modulus of the acetal homopolymer (trademark Delrin) is approximately 380,000 psi and has been found suitable, as have the other materials mentioned above, for providing the desired deflection over the specified load levels. The range of loading from 200 to 450 pounds is a design parameter corresponding to two and one-half times the body weight of the user, which represents typical loads during running and jumping. In addition to these mentioned properties, the material should be relatively light in weight, i.e. less than most metals, so as to minimize the weight of the complete foot, including the foamed polymer cover and attachment fittings. All of these properties are found in the above-mentioned group of polymers.

In the currently perferred embodiment of keel 12, the hardened polymer is selected from the above group and used without fiber reinforcement in order to not counteract the viscous properties of such material which cause the desired dampening. Fiber reinforcement can be used to make a sufficiently strong keel from lighter weight polymers but care must be taken in selecting fiber materials that are either visco-elastic themselves or in deploying the fibers at random orientations. An example of the former is to use organic fibers such as aromatic polyamides (available under the tradename Kevlar from Dupont Corporation) which have a characteristically greater visco-elastic property than such inorganic fibers as glass or carbon. Such organic reinforcing fibers can be used in relatively lightweight reaction injection molded polymers for making the keel strong enough and without loss of dampening.

Figure 2:
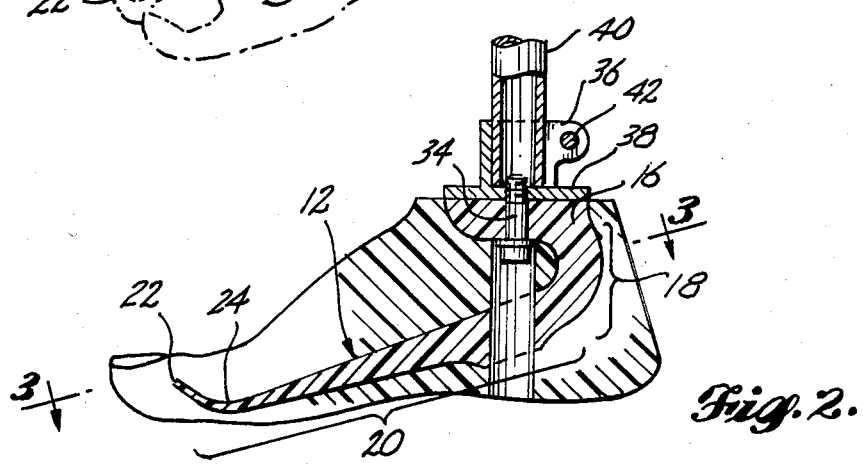
FIG. 2 is a lengthwise, vertical sectional view of the foot of FIG. 1, with the cover shown in solid lines, and with the addition of an attachment bolt and split collar fitting for clamping the foot to a prosthetic pylon.
Figure 3:
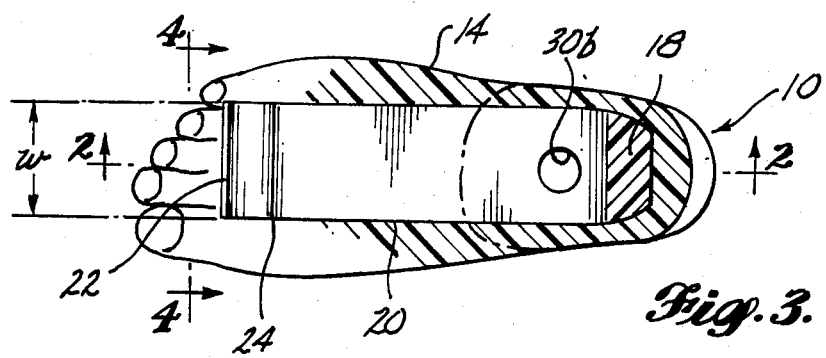
FIG. 3 is a sectional view of the foot, taken along the plane indicated by reference line 3—3 of FIG. 2.

With reference to FIGS. 2, 3 and 5, heel portion 18 elongate and is relatively thickened and smoothly curved for uniform stress, and is shaped and arranged so as to carry the body load first downward and rearward from the attachment flange, and then curve downward and, finally, downward and forward, blending into the forefoot portion 20. Locating heel portion 20 beneath the rear extent of flange 16 places the apparent center of rotation of the foot close to the natural ankle position. The relatively thickened cross section of heel portion 18 (see FIG. 3), is roughly rectangular and the relatively large radius of curvature on the forward and rear surfaces, compensate for the larger stresses that occur in this region relative to other areas of the keel 12, resulting in a keel body that is shaped for uniform distribution of stress over the entire keel body. Such a uniform distribution of the stress significantly lengthens the fatigue life of the keel while, at the same time providing the crucial deflection-to-load relationship mentioned above and the minimal weight of the complete foot. Also, by arranging the heel portion 18 so as to carry the load around the area through which the industry standard attachment bolt passes, the fatigue life of the keel is further enhanced by reducing stress concentrations which would occur by reason of the bolt clearance hole cutting partially through the heel portion 18.

With reference to FIG. 5, the uniform stress throughout the keel is achieved by judicious shaping of the heel portion 18 where, because of the curvature, the highest stresses are encountered. Specifically, the ratio of the radius R (measured from the center of curvature to the path 25 of the centroidal axis of portion 18) to the thickness C of material between the centroidal axis 25 and the inside curved surface of heel portion 18 is selected so as to keep the stress level in the heel region to no greater than substantially 2.5 times that of the corresponding stress level exhibited by a straight beam of the same thickness.

The forefoot portion 20 is formed with a parabolic taper (FIG. 5) so as to increase the rate of deflection as a function of load adjacent to the toe end. By so doing, keel 12 can be made shorter, while still providing adequate deflection for the lightest of loads and without exceeding the maximum possible deflection for the heaviest of anticipated loads. Furthermore, by maintaining the upper surface 20a of forefoot 20 flat and placing the curvature of the parabolic taper on the lower surface 20b, the unit tensile strain on the bottom surface of the keel is reduced at required deflection so as to prolong the fatigue life of the keel material.

The upturn of foot portion 20 adjacent toe end 22 minimizes the required deflection angle of the keel when the angle of the leg axis is less than 90 degrees to the ground plane (see FIG. 6). The upturn at the toe end 22 also assists in transferring horizontal loads to the keel from the foamed cover at minimum bond line stress. During use, contact between the ground and a shoe worn on the prosthetic foot, stresses cover 18 which, in turn, must pass such stress on to keel 12, and the upturned end of forefoot 20 provides a vertical component in the cover-to-keel bond so as to pass horizontal loads without damage to the bond lines lying along the generally horizontal main body portion of forefoot 20. The thickness of forefoot 20 beyond the toe break 24 out to the toe end 22, must be kept thin enough to allow angular deflection during toe flexure without exceeding allowable fatigue stress levels.

Cover 14 is preferably a flexible cellular polymer, such as polyurethane, molded or otherwise shaped to the form of a natural foot, such as by casting from the natural foot. This cover must be of a material capable of withstanding many cycles of compression from heel strike and flexing in the material surrounding forefoot 20 out to toe break 22. Additionally, the material must withstand surface abrasion from socks and shoes during years of vigorous usage by the amputee. Furthermore, the material of cover 14 must be compatible with the polymer used to form keel 12 and, particularly, the cover material must bond to the exterior surface of keel 12 so that loads, especially horizontal loads, are passed faithfully from cover 14 to keel 12, as discussed above.

In the preferred embodiment shown in FIGS. 1 through 6, foot 10 is formed with vertically aligned through bores 30a and 30b, the former being located centrally of attachment flange 16 and being of slightly smaller diameter, and the latter extending upwardly from the foot bottom 32 of cover 14 (see FIG. 2) for passing the head of a standard attachment bolt 34 up to a position where the bolt head seats against the shoulder of the smaller bore hole 30a in flange 16. A standard industry fitting 36, in this instance being of the split collar clamping type, is held in place by threading bolt 34 to an interiorly threaded base flange 38 of fitting 36, as illustrated in FIGS. 2 and 6. Fitting 36, in turn, receives a standard prosthetic pylon 40, or similarly shaped prosthesis, and a clamping screw indicated at 42 of fitting 36 secures pylon 40 to fitting 36 and, hence, to keel 12. The thickness dimension of attachment flange 16 is selected in light of the other properties of the keel material mentioned above, so that flange 16 has some flexibility in the horizontal plane in order to assit in providing the overall required deflection between pylon 40 and the load point (corresponding to the ball of the foot) on the bottom of forefoot portion 20, without causing excessive prying loads on bolt 34. Without such flexibility of keel flange 16, prying loads on the bolt 34 would result in its premature failure.

Also, to accommodate the portion of through bore 30b that passes through the foot portion 20 of keel 12, without exceeding stress level concentrations on the keel in this region, the thickness portion 20 is increased in the region surrounding bore 30a, as best shown in FIG. 2.

In the preferred method of manufacturing prosthetic foot 10, keel 12 is formed by a thermoplastic injection molding process, although thermoset molding can also be used. While the length and thickness dimensions of the keel will vary, depending upon the weight range of the patients for which different production runs of the foot are made, examples of two different models are indicated. In a first model, made for patients weighing between 100 and 160 pounds, the forefoot 20 of keel 12 has a beam length (measured horizontally between toe break 24 and the center line of attachment bolt bore holes 30a and 30b) of 4.5 inches and a deflection that varied from 0.7 inches for a 200 pound force to about 1.5 inches for a 500 pound force wherein the deflection is a measure of the displacement of the forefoot between its strained and unstrained conditions at the ball of the foot, as indicated by arrow 29 in FIG. 6. The weight of this first keel model was about 210 grams and was made of acetal homopolymer. For the second model, intended for patients weighing between 160 and 200 pounds, the beam length was also 4.5 inches, but the deflection rate varied from 0.75 inches at 200 pounds to 1.8 inches at 500 pounds. The different deflection rates were obtained by changing the thickness t of the beam of forefoot portion 20, as shown in FIG. 5. The keel material was an acetal homopolymer and this model weighed 220 grams. The maximum and uniform bending stress on the first keel (weights 120 to 160 pounds) was 12,781 psi and, for the heavier weight model (weights 161 through 200 pounds), the maximum and uniform bending stress was 13,775 psi. These maximum bending stresses were within the manufacturer's stated limits of this acetal homopolymer. The deflection of the monolithic keels at the design loads were compared with corresponding deflections of laminate keels at the same loads, and it was established that the monolithic keel achieved deflections that were from 50 percent to over 200 percent greater than deflections achieved by laminate beam structures.

After the keel is formed, the foamed polymer cover is molded to the keel. The foam material may be chosen from a number of suitable products commercially available, such as a polyester MDI urethane. The "cream time" of the foam should be at least 30 seconds when a hand-poured method is used, as was the case in this example. Foam densities in the range of 25 to 30 pounds per cubic foot were achieved for these examples, however, other foam materials and processes may be available for reducing the final density to the range of 10 to 15 pounds per cubic foot. The lower density is desired in order to reduce the overall weight of the foot. In the two models described here, our method of fabrication resulted in the complete foot model weighing about 1.25 pounds, including the cover.

With reference to FIG. 7, an alternate embodiment of the invention is illustrated in which the forefoot portion 20' is slit lengthwise, as indicated at 60, between the toe end 22' and a location forward of the heel portion 18'. In the illustrated embodiment, the forefoot is slit three times to form a plurality of four independently deflectable toe-like segments 61, 62, 63 and 64. As depicted in FIG. 7a, the provision of such independently deflectable toe-like segments 61–64 improves the stability of the foot when traversing uneven surfaces, by allowing the toe segments to deflect as indicated over an obstacle 70 which does not span the full width of the forefoot. A similar advantageous effect results when walking on a transversely sloping surface. A further advantage of the slit forefoot is to provide some flexibility from side-to-side, i.e., rotation of the foot in the horizontal plane about a vertical axis through the ankle. Thus, the toe-like segments can deflect in the horizontal plane, a few degrees relative to the fixed ankle connection and, thereby, provide torsional movement of a few degrees, as encountered in a normal foot and gait. The number of slits 60 and, hence, toe segments 61 through 64 can be varied, and we recommend either four or five such toe segments.

FIG. 8 shows a further alternative embodiment, in which the monolithic keel 12" of foot 10" is also formed with an integral heel spur 80 that extends rearward and downward from the keel 12", substantially where the heel portion 18 turns into the forefoot portion 20". The heel spur 80, being of the same hardened polymer material as the keel itself, has elastic and viscous properties which, like the keel, provide for energy storage and timed (lagging) recovery of such energy on each heel strike and rebound therefrom. The dotted line moved position of heel spur 80, shown in FIG. 8, shows the upward deflection of the spur in reaction to a heel strike force, indicated by arrow 82. Also, the heel spur 80 provides added stiffness to the complete foot 10" when lighter and softer foamed covers 14 are employed, since the cover in such case may not provide sufficient absorption of heel impact loads. Additionally, the energy recovery from the heel spur 80 assists the user in providing heel uplift in reaction to the heel strike which, in turn, forces the forefoot downward into an energy-storing deflection for the subsequent primary uplift and forward thrust of the foot.

FIGS. 9 and 10 show an alternative embodiment in which the monolithic keel 12''' is formed with an integral attachment fitting 90. Attachment fitting 90 is in the configuration of a split collar, similar to one of the industry standard fittings available as a separate component, but here molded integrally with the lightweight polymer keel 12'''. Fitting portion 90 extends upwardly as a cylindrical collar from the attachment flange portion 16''', such that the bottom of the pylon receiving opening 92 of fitting portion 90 is at the upper, central surface of flange portion 16'''. Fitting portion 90 is split in the vertical dimension, as indicated at 94, and a conventional clamping fastener 96 is provided as in the case of the above-described conventional clamp fitting 36, shown in FIG. 2. Fitting portion 90 saves weight and cost of providing the industry standard separate metal, split collar fitting.

FIG. 11 shows a keel 12''' with another type of integral attachment fitting in the shape of a stub 96 projecting upward from the center of the flange portion and adapted to receive a matching prosthetic fitting.

It is thus seen that the invention provides a monolithic hardened polymer keel, disposed as a cantilever spring that is uniquely shaped for minimal and uniformly distributed stress levels, so that the weight of the keel and overall foot can be kept to a comfortable minimum. The material selected for the keel has a mix of both viscous and elastic properties so that the deflection and recovery, which respectively store and return footfall energy to the user, occur at a timed or lagging rate so that the rebound of the foot takes place at a natural rate, rather than being too rapid and thereby "rushing" the amputee. A flexible, foamed cellular polymer covers the keel and provides both structural (load transfer) and cosmetic benefits.

While only particular embodiments have been disclosed herein, it will be readily apparent to persons skilled in the art that numerous changes and modifications can be made thereto, including the use of equivalent means, devices and method steps, without departing from the spirit of the invention.

The embodiments of the invention in which an exclusive property or privilege is defined, are claimed as follows:

1. A prosthetic foot comprising:
   a cantilever spring monolithic keel of hardened polymer having visco-elastic properties, and a cover encasing said keel, said keel having an attachment means adapted for connection to an upper prosthesis and having strain energy storing forefoot and heel portions, said heel portion being a curved, bendable transition that joins said forefoot portion to said attachment means and transfers loads therebetween, said attachment means, curved heel portion, and forefoot portion being shaped and dimensioned to have substantially uniform bending stress distribution and strain energy storage throughout said keel for storing strain energy associated with each footfall and returning such energy as footlift and thrust with the following footrise.

2. The prosthetic foot of claim 1, wherein said cover comprises a foamed polymer that is bonded to said hardened polymer of said keel.

3. The prosthetic foot of claim 1, wherein attachment means of said keel comprises an ankle attachment flange and said heel portion has a centroidal axis that extends downward and rearward from said attachment flange and then curves to a downward and forward direction, and said forefoot portion extends from said heel portion at a downward and forward slope toward a toe end.

4. The prosthetic foot of claim 1, wherein said forefoot portion of said keel is slit lengthwise into a plurality of toe-like segments.

5. The prosthetic foot of claim 1, wherein said keel is formed with an integral spring heel spur that extends downward and rearward from said heel portion, said heel spur reacting to each heel strike of a footfall to store strain energy and return such energy as heel lift with the following footrise.

6. The prosthetic foot of claim 3, wherein said heel portion curves at a radius R measured from the center of curvature to a path of said centroidal axis of said heel portion, said heel portion in cross section defines a dimension C measuring the partial thickness along said radius R between said centroidal axis and a surface of said heel portion adjacent said center of curvature, and wherein said radius R and partial thickness dimension C are selected to have a ratio of R/C that results in stress concentration in said curved heel portion of said keel of no greater than 2.5 times that of a straight beam of the same thickness.

7. The prosthetic foot of claim 6, wherein said heel portion is shaped so as to be generally rectangular or trapezoidal in cross section taken transversely through the centroidal axis.

8. The prosthetic foot of claim 1, wherein said hardened polymer is selected from the group consisting essentially of acetal homopolymer, polyether ether ketone and polyamide-imide.

9. The prosthetic foot of claim 1, wherein said hardened polymer is reinforced by fibers.

10. The prosthetic foot of claim 9, wherein said fibers are made of an organic material having a visco-elastic property.

11. The prosthetic foot of claim 10, wherein said organic material is an aromatic polyamide.

12. The prosthetic foot of claim 1, wherein said forefoot portion of said keel has a thickness that varies as a parabolic taper adjacent the toe end.

13. The prosthetic foot of claim 1, wherein said forefoot portion of said keel slopes forward and downward from said heel portion and terminates at a toe end.

14. The prosthetic foot of claim 13, wherein said forefoot portion has a thickness that varies as a parabolic taper adjacent the toe end.

15. The prosthetic foot of claim 14, wherein the forefoot portion has a generally uniform width and said thickness that varies as a parabolic taper is measured between upper and lower surfaces of said forefoot portion.

16. The prosthetic foot of claim 15, wherein the upper surface of said forefoot portion is generally planar and the lower surface is shaped so as to form said thickness that varies as a parabolic taper.

17. The prosthetic foot of claim 14, wherein said forefoot portion has a widthwise break in the foreward and downward slope adjacent said toe end, where said forefoot bends upward and forward to said toe end.

18. A method of fabricating a prosthetic foot for a patient having a body weight within a specified range, comprising:
   forming a monolithic cantilever spring keel with forefoot, curved heel transition and ankle attachment portions from a hardened polymer, selected to have visco-elastic properties for combined strain energy storage and dampened energy release, said material having a predetermined maximum bending stress;
   shaping and dimensioning said keel portions so as to have substantially uniform bending stress distribution and strain energy storage throughout said portions of said keel, and to have a visco-elastic deflection within the range of substantially 0.7 to 1.8 inches measured between the ankle attachment portion and a position on said forefoot portion of said keel corresponding to the ball portion of a natural foot when under a load of 2½ times the patient's body weight, and so that said deflection does not cause said predetermined maximum bending stress to be exceeded; and encasing said keel in a foamed polymer that is bonded to said hardened polymer.

19. The method of claim 18, wherein said hardened polymer is selected from the group consisting essentially of acetal homopolymer, polyether ether ketone and polyamide-imide.

20. A keel for a prosthetic foot comprising:

a cantilever spring monolithic member made of hardened polymer having visco-elastic properties, said cantilever spring member having an attachment means adapted for connection to an upper prosthesis, a forefoot portion, and an elongate curved heel portion that is a strain energy storing transition between said forefoot portion and said attachment means, said heel and forefoot portions shaped for substantially uniform bending stress distribution and for storing strain energy throughout said member in reaction to each footfall and returning such energy as footlift and thrust with the following footrise.

21. The prosthetic foot of claim 1, wherein said heel portion has a centroidal axis that uniformly curves between said attachment means and said forefoot portion in a downward and rearward direction from said attachment means and then in an downward and forward direction to said forefoot portion.

22. The prosthetic foot of claim 21, wherein said heel portion has a thickness in the plane of curvature of said centroidal axis that is substantially uniform along said centroidal axis.

23. The prosthetic foot of claim 22, wherein said centroidal axis of said heel portion has a curvature of radius R, and said thickness of said heel portion in said plane of said curvature has a dimension C measuring the partial thickness along the radius R between said centroidal axis and a surface of said heel portion adjacent the center of curvature, and wherein said radius R and partial thickness dimension C are selected to have a ratio of R/C that results in stress concentration in said curved heel portion of no greater than 2.5 times that of a straight beam of the same thickness.

24. A prosthetic foot comprising:

a cantilever spring keel of hardened polymer having visco-elastic properties, and a cover encasing said keel, said keel having means adapted for connection to an upper prosthesis and having a forefoot portion and an elongate curved heel portion that provides a strain energy storing structural transition between said forefoot portion and said means adapted for connection to an upper prosthesis, said heel and forefoot portions dimensioned and shaped to have substantially uniform stress and uniform strain energy storage throughout said heel and forefoot portions for storing strain energy associated with each footfall and returning such strain energy as footlift and thrust with the following foot rise.

25. The prosthetic foot of claim 24, wherein said hardened polymer has a predetermined bending stress limit, and wherein said keel is dimensioned and shaped to have uniform bending stress within said predetermined bending stress limit of said hardened polymer.

26. The prosthetic foot as set forth in claim 24, for a user having a body weight within a specified weight range, wherein:

said hardened polymer has a predetermined maximum bending stress limit and said means adapted for connection to an upper prosthesis and said heel and forefoot portions are sized and shaped so as to have a range of visco-elastic deflections from substantially 0.7 inches to 1.8 inches measured between said ankle attachment means and a position on said keel corresponding to the ball of a natural foot in reaction to a range of loads on the foot equal to 2½ times the body weight within said specified weight range, said keel when so loaded and deflected having substantially uniform bending stress in said heel and forefoot portions that is less than said predetermined maximum bending stress limit.

* * * * *